United States Patent
Logan et al.

(10) Patent No.: US 11,980,557 B2
(45) Date of Patent: May 14, 2024

(54) STENT DELIVERY SYSTEMS

(71) Applicant: BOSTON SCIENTIFIC SCIMED, INC., Maple Grove, MN (US)

(72) Inventors: Brady Scott Logan, Maple Grove, MN (US); Paul Goudreau, Edina, MN (US); Ian Forte, Brooklyn Park, MN (US); Andrew Smith, Brooklyn Center, MN (US); Tyler Hebig, Wayzata, MN (US); Ryan Hendrickson, Albertville, MN (US); Derek Kenneth Larson, Golden Valley, MN (US); Jason T. Anderson, Deephaven, MN (US); Rowan Olund Hettel, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/825,040

(22) Filed: May 26, 2022

(65) Prior Publication Data

US 2022/0280319 A1    Sep. 8, 2022

Related U.S. Application Data

(63) Continuation of application No. 17/062,243, filed on Oct. 2, 2020, now Pat. No. 11,364,136.
(Continued)

(51) Int. Cl.
*A61F 2/966* (2013.01)
*A61B 17/00* (2006.01)

(52) U.S. Cl.
CPC ............ *A61F 2/9661* (2020.05); *A61B 17/00* (2013.01); *A61B 2017/00367* (2013.01); *A61B 2017/00477* (2013.01)

(58) Field of Classification Search
CPC .......... A61B 17/00; A61B 2017/00367; A61B 2017/00477; A61F 2/9517; A61F 2/966; A61F 2/9661; A61F 2/962; A61F 2/9522
See application file for complete search history.

(56) References Cited

U.S. PATENT DOCUMENTS

| | | |
|---|---|---|
| 5,882,333 A | 3/1999 | Schaer et al. |
| 6,402,760 B1 | 6/2002 | Fedida |

(Continued)

FOREIGN PATENT DOCUMENTS

| | | |
|---|---|---|
| DE | 202018101750 U1 | 4/2018 |
| EP | 1518516 A1 | 3/2005 |

(Continued)

OTHER PUBLICATIONS

International Search Report and Written Opinion dated Feb. 22, 2021 for International Application No. PCT/US2020/054067.

*Primary Examiner* — Jocelin C Tanner
(74) *Attorney, Agent, or Firm* — Seager, Tufte & Wickhem, LLP

(57) ABSTRACT

Stent delivery systems and methods for making and using stent delivery systems are disclosed. An example stent delivery system may include an inner member having a stent receiving region, a stent disposed along the stent receiving region, a deployment sheath axially slidable relative to the inner member, the deployment sheath having a proximal end region, a handle coupled to the deployment sheath, a rod coupled to the handle, the rod having a distal end region, a proximal end region and a first threaded portion extending from the distal end region to the proximal end region and a coupling member configured to couple the rod to the deployment sheath, the coupling member having an engagement portion. Additionally, the first threaded portion of the rod is designed to engage the engagement portion of coupling (Continued)

member and rotation of the rod is designed to translate the coupling member along the rod.

18 Claims, 15 Drawing Sheets

Related U.S. Application Data

(60) Provisional application No. 62/910,786, filed on Oct. 4, 2019.

(56) References Cited

U.S. PATENT DOCUMENTS

| | | | |
|---|---|---|---|
| 6,923,813 B2 | 8/2005 | Phillips et al. | |
| 7,285,130 B2 | 10/2007 | Austin | |
| 8,784,468 B2 | 7/2014 | Gerdts et al. | |
| 9,084,692 B2 | 7/2015 | Hacker et al. | |
| 9,220,619 B2 | 12/2015 | Ramos et al. | |
| 10,292,744 B2 | 5/2019 | Santangelo et al. | |
| 10,369,338 B2* | 8/2019 | Berkowitz | A61B 17/3421 |
| 10,441,449 B1* | 10/2019 | Longo | A61F 2/966 |
| 2010/0049313 A1 | 2/2010 | Alon et al. | |
| 2012/0172963 A1 | 7/2012 | Ryan et al. | |
| 2012/0185031 A1 | 7/2012 | Ryan et al. | |
| 2012/0330401 A1* | 12/2012 | Sugimoto | A61F 2/915 623/1.12 |
| 2013/0123898 A1* | 5/2013 | Tung | A61F 2/2436 623/1.11 |
| 2015/0051688 A1* | 2/2015 | Cummins | A61F 2/9517 623/1.11 |
| 2015/0057739 A1* | 2/2015 | Costello | A61F 2/9517 623/1.11 |
| 2015/0265445 A1* | 9/2015 | Weber | A61F 2/966 623/1.12 |
| 2015/0282881 A1 | 10/2015 | Beard et al. | |
| 2016/0120677 A1 | 5/2016 | Heanue et al. | |
| 2016/0128857 A1 | 5/2016 | Kao | |
| 2017/0325954 A1 | 11/2017 | Perszyk | |

FOREIGN PATENT DOCUMENTS

| | | |
|---|---|---|
| EP | 3005983 A1 | 4/2016 |
| JP | H10500334 A | 1/1998 |
| JP | 2001145700 A | 5/2001 |
| JP | 2007503911 A | 3/2007 |
| JP | 2014533190 A | 12/2014 |
| JP | 2015513979 A | 5/2015 |
| JP | 2017510369 A | 4/2017 |
| WO | 2013074662 A1 | 5/2013 |
| WO | 2015153887 A2 | 10/2015 |

* cited by examiner

STENT DELIVERY SYSTEMS

CROSS-REFERENCE TO RELATED APPLICATIONS

This application is a continuation of U.S. Non-Provisional application Ser. No. 17/062,243, filed Oct. 2, 2020, which claims the benefit under 35 U.S.C. § 119 to U.S. Provisional Application Ser. No. 62/910,786, filed Oct. 4, 2019, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A stent delivery system is disclosed. The stent delivery system includes an inner member having a stent receiving region, a stent disposed along the stent receiving region, a deployment sheath axially slidable relative to the inner member, the deployment sheath having a proximal end region, a handle coupled to the deployment sheath, a rod coupled to the handle, the rod having a distal end region, a proximal end region and a first threaded portion extending from the distal end region to the proximal end region and a coupling member configured to couple the rod to the deployment sheath, the coupling member having an engagement portion. Additionally, the first threaded portion of the rod is designed to engage the engagement portion of coupling member and rotation of the rod is designed to translate the coupling member along the rod.

Alternatively or additionally to any of the embodiments above, wherein the engagement portion of the coupling member includes a second threaded portion.

Alternatively or additionally to any of the embodiments above, wherein the first threaded portion includes an external thread, and wherein the second threaded portion includes an internal thread, and wherein the external thread is configured to engage with the internal thread.

Alternatively or additionally to any of the embodiments above, wherein the engagement portion of the coupling member includes at least one projection extending radially outward from an outer surface of the coupling member.

Alternatively or additionally to any of the embodiments above, wherein the first threaded portion includes an internal thread, and wherein the at least one projection of the coupling member is configured to engage with the internal thread.

Alternatively or additionally to any of the embodiments above, wherein the coupling member is configured to translate along the rod from the distal end region to the proximal end region, and wherein the translation of the coupling member pulls the deployment sheath proximally to deploy the stent.

Alternatively or additionally to any of the embodiments above, wherein coupling member is configured to translate relative to the inner member.

Alternatively or additionally to any of the embodiments above, wherein the coupling member includes an aperture, and wherein the inner member is designed to extend within the aperture.

Alternatively or additionally to any of the embodiments above, wherein the coupling member further includes a flange, and wherein handle includes a channel extending along a longitudinal axis of the handle, and wherein the flange is designed to engage with the channel.

Alternatively or additionally to any of the embodiments above, wherein the coupling member includes a bottom surface, and wherein the bottom surface substantially aligns with a midline of the rod.

Alternatively or additionally to any of the embodiments above, wherein the handle further comprises a thumbwheel coupled to both the handle and the rod, and wherein actuation of the thumbwheel is configured to rotate the rod.

Alternatively or additionally to any of the embodiments above, wherein the handle includes an inner chamber, and wherein both the rod and the coupling member are disposed within the inner chamber.

Another stent delivery system includes an inner member having a stent receiving region, a stent disposed along the stent receiving region, a deployment sheath axially slidable relative to the inner member, a handle coupled to the deployment sheath, a rod coupled to the handle, the rod having a distal end region, a proximal end region and a first threaded portion extending from the distal end region to the proximal end region and a coupling member configured to couple the rod to the deployment sheath, the coupling member having a second threaded region configured to engage the first threaded portion of the rod, wherein rotation of the rod is designed to shift the coupling member from a first configuration in which the deployment sheath covers the stent to a second configuration in which the deployment sheath uncovers the stent.

Alternatively or additionally to any of the embodiments above, wherein shifting the coupling member from the first configuration to the second configuration includes proximally retracting the coupling member relative to the rod.

Alternatively or additionally to any of the embodiments above, wherein the coupling member includes an aperture, and wherein the inner member is designed to extend within the aperture.

Alternatively or additionally to any of the embodiments above, wherein the coupling member further includes a flange, and wherein handle includes a channel extending along a longitudinal axis of the handle, and wherein the flange is designed to engage with the channel.

Alternatively or additionally to any of the embodiments above, wherein the coupling member includes a bottom surface, and wherein the bottom surface substantially aligns with a midline of the rod.

Alternatively or additionally to any of the embodiments above, wherein the handle further comprises a thumbwheel coupled to both the handle and the rod, and wherein actuation of the thumbwheel is configured to rotate the rod.

Alternatively or additionally to any of the embodiments above, wherein the handle includes an inner chamber, and wherein both the rod and the coupling member are disposed within the inner chamber.

An example method for deploying a stent includes advancing a stent delivery system to a target site, the stent delivery system including: an inner member having a stent receiving region, a stent disposed along the stent receiving region, a deployment sheath axially slidable relative to the inner member, the deployment sheath having a proximal end region, a handle coupled to the deployment sheath, the handle including an actuation member, a rod coupled to the handle, the rod having a distal end region, a proximal end region and a first threaded portion extending from the distal end region to the proximal end region and a coupling member configured to couple the rod to the deployment sheath, the coupling member having an engagement portion disposed along the coupling member; wherein the first threaded portion of the rod is designed to engage the engagement portion of coupling member. The method also includes actuating the actuation member, whereby actuation of the actuation member rotates the rod, and wherein rotating the rod translates the coupling member along the rod, and wherein translating the coupling member shifts the deployment sheath from a first position in which the stent is covered to a second position in which the stent is uncovered.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
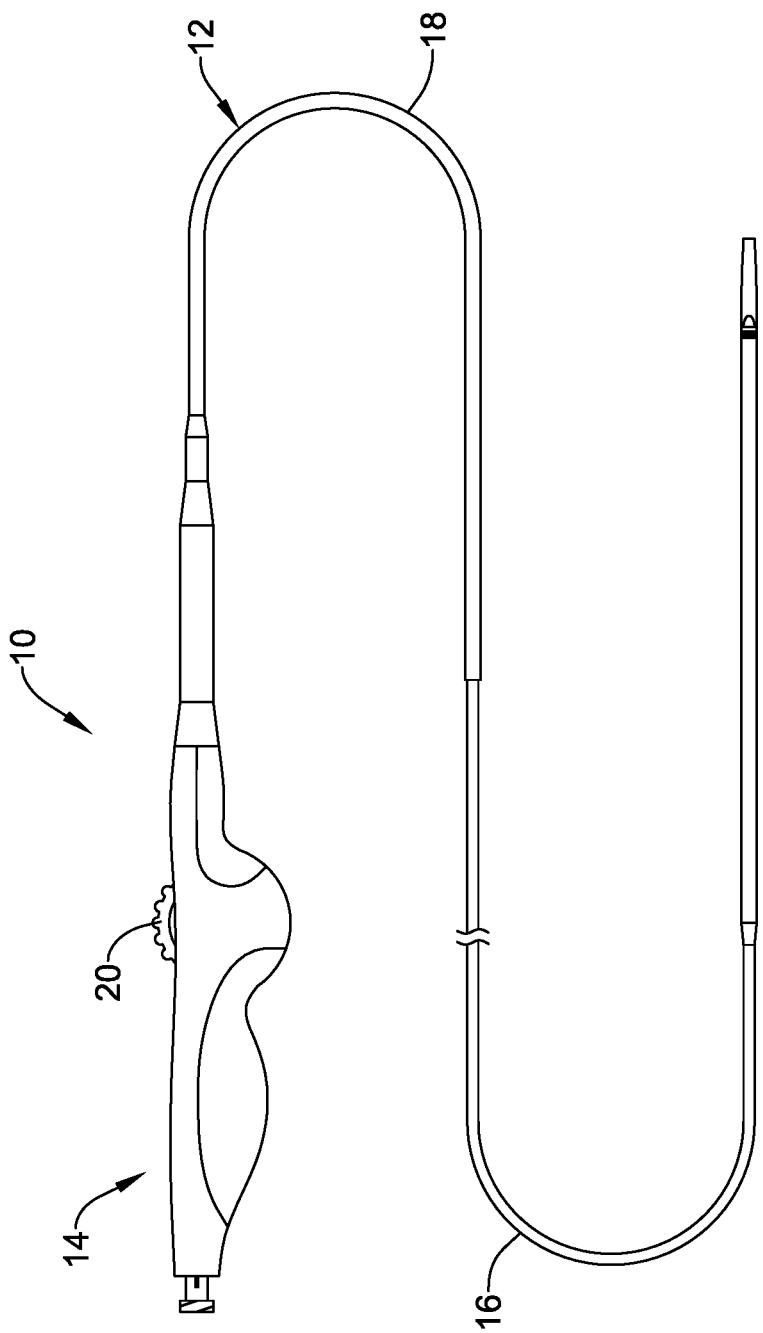
FIG. 1 is a side view of an example stent delivery system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

FIG. 1 illustrates an example stent delivery system 10. The system 10 may include an elongate shaft 12 and a handle 14 coupled to the shaft 12. The shaft 12 may include an inner shaft or liner (not shown in FIG. 1, can be seen in FIG. 2), a deployment sheath 16, and an outer shaft 18. In general, the system 10 may be used to deliver a stent, graft, endoprosthesis or the like to an area of interest within a body lumen of a patient. The body lumen may be a blood vessel located near the heart (e.g., within or near a cardiac vessel), within a peripheral vessel, within a neurological vessel, or at any other suitable location. Deployment of the stent may include proximal retraction of a deployment sheath 16, which overlies or otherwise is designed to cover the stent during delivery of the stent. Retraction of the deployment sheath 16 may include the actuation of an actuation member 20 generally disposed at the handle 14. In the example illustrated in FIG. 1, the actuation member 20 is a thumb wheel that can be rotated by a clinician in order to accomplish proximal retraction of the deployment sheath 16. Numerous other actuation members are contemplated.

Figure 2:
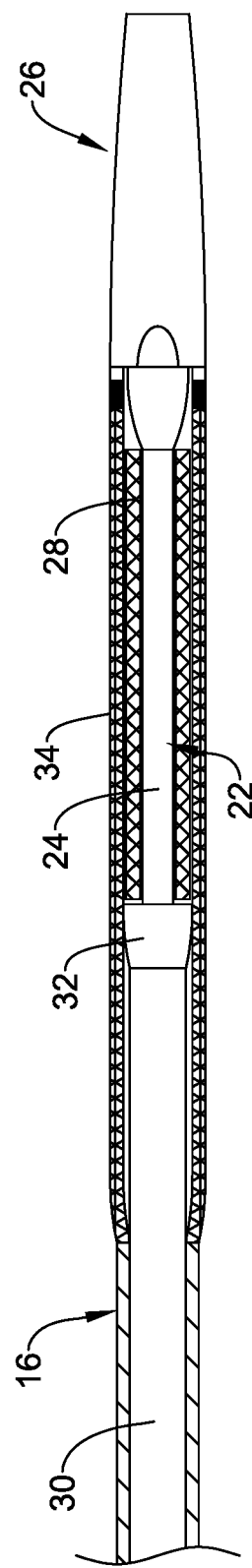
FIG. 2 illustrates a portion of an example stent delivery system.

Some of the other features of the system 10 are shown in FIG. 2. For example, the system 10 may include an inner member 22. The inner member 22 may define a guidewire lumen and may include a stent receiving region 24 about which a stent 28 may be disposed. In at least some instances, the stent 28 is a self-expanding stent and may be made from a suitable material such as a nickel-titanium alloy. A distal tip 26 may be attached to or otherwise disposed at the distal end of the inner member 22. The distal tip 26 may generally have a rounded or smooth shape that provides a generally atraumatic distal end to system 10. A bumper shaft or member 30 may be disposed about the inner member 22. The bumper shaft 30 may include a bumper region 32. In general, the bumper region 32 may function as a proximal bumper during deployment of the stent 28. Also depicted in FIG. 2 is that the deployment sheath 16 may include an enlarged distal section 34. In some instances, the system 10 may include features of the systems disclosed in U.S. Pat. Nos. 8,784,468, 9,084,692, and 9,220,619, the entire discloses of which are herein incorporated by reference.

Stent delivery systems are typically used along with a guidewire (e.g., the systems typically threaded over a guidewire). It may be desirable for a clinician to maintain the position of the guidewire relative to the system (e.g., relative to the handle). It may also be desirable to reduce the likelihood that the guidewire may become kinked, for example at locations adjacent to the handle. The systems disclosed herein are designed to allow a clinician to maintain the position of the guidewire relative to the handle, reduce the likelihood of kinking the guidewire adjacent to the handle, and the like. Other features are also contemplated.

Figure 3:
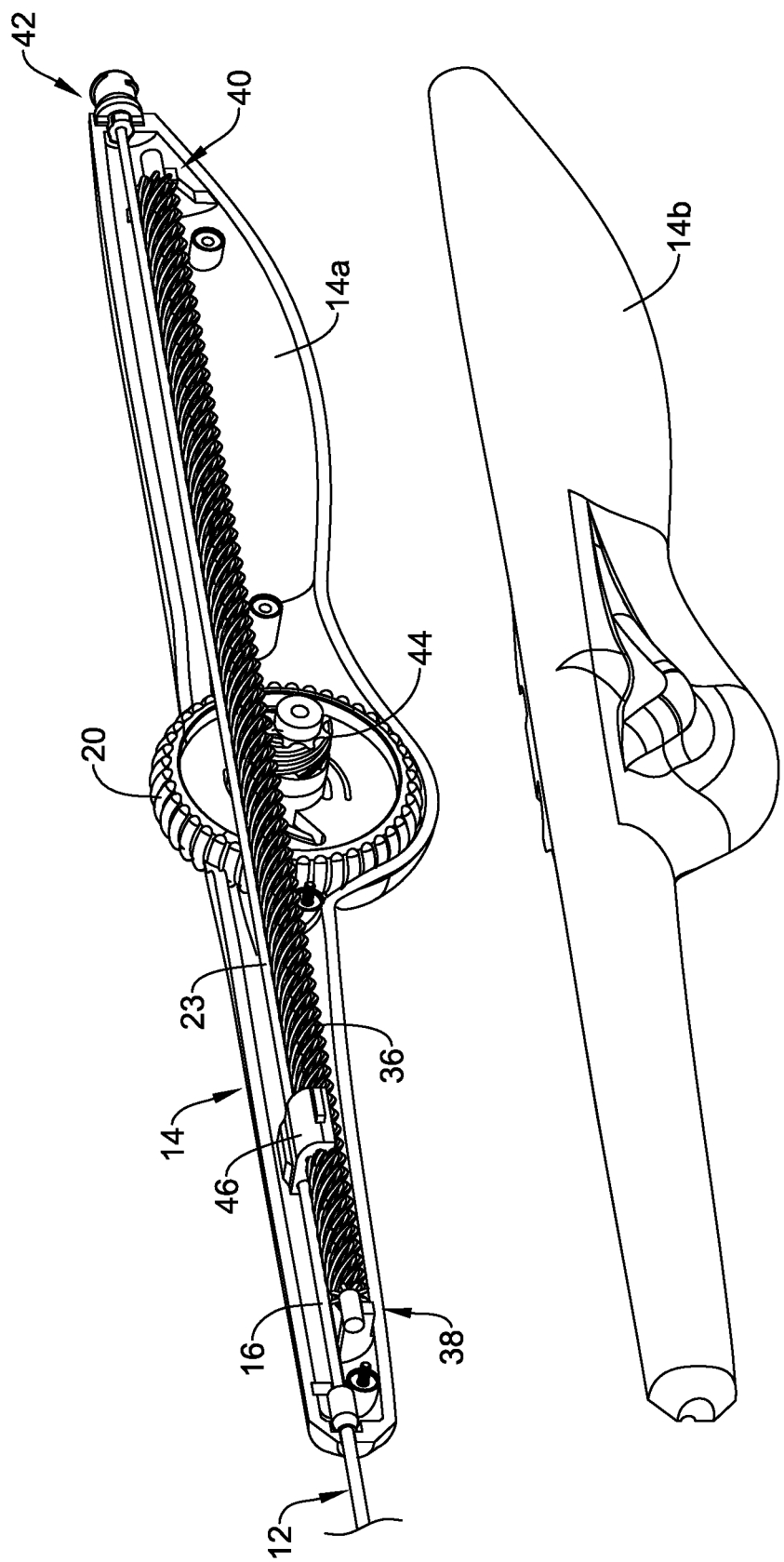
FIGS. 3-6 illustrate a portion of an example stent delivery system.

As shown in FIG. 3, the deployment sheath 16 may be coupled to a threaded rod 36 via a coupling member 46 (described in greater detail below). For example, a proximal end of the deployment sheath 16 may be coupled to (e.g., fixedly attached to) the coupling member 46. Further, the coupling member 46 may include an engagement portion (e.g., internal threads) that engage with the external threads of the threaded rod 36, thereby coupling the deployment sheath 16 to the threaded rod 36.

Additionally, FIG. 3 illustrates that the system 10 may further include an inner shaft 23 (e.g., hypotube). The inner shaft 23 may extend within both a lumen of the deployment sheath 16 and an aperture of the coupling member 46. For example, as will be described in greater detail below, the inner shaft 23 may exit the lumen of the deployment sheath 16 at a position adjacent the coupling member 46, whereby the inner member may then pass through an aperture (discussed below) of the coupling member 46 and extend to the proximal end region 42 of the handle 14. Additionally, in some examples, the inner shaft 23 may be attached to the inner member 22. However, in yet other examples, the inner shaft 23 and the inner member 22 may be a monolithic component. In other words, in some examples the inner shaft 23 and the inner member 22 may include a shaft attached to a hypotube, respectively. However, in other examples, the inner shaft 23 and the inner member 22 may be a single, monolithic tubular component.

As discussed above, the threaded rod 36 may include an external thread extending helically from first end region 38 of the rod to a second end region 40 of the rod. In general, the threaded rod 36 may be disposed within the handle 14 such that the handle 14 allows for the threaded rod 36 to rotate while being contained within the handle 14 (e.g., in a manner such that the threaded rod 36 does not exit the handle 14 when in either an initial or first configuration or when in other configurations including those where the deployment sheath 16 is retracted in order to deploy the stent 28). This arrangement may provide greater access to a guidewire extending through the system 10 (e.g., and out from a proximal end 42 of the handle 14) and allow a clinician to maintain the position of the guidewire relative to the system 10 and to reduce/avoid kinking the guidewire.

In some examples, rotation of the threaded rod 36 may result in movement of the deployment sheath 16 (e.g., which may include proximal retraction of the deployment sheath 16 and/or deployment of the stent 28). Specifically, rotation of the threaded rod 36 may translate the coupling member 46 in a distal-to-proximal direction (via engagement of the external threads of the rod 36 with the internal threads of the coupling member 46). Further, because the deployment sheath 16 is attached to the coupling member 46, the distal-to-proximal translation of the coupling member 46 may "pull" the deployment sheath 16 in a distal-to-proximal direction. Additionally, in order to rotate the threaded rod 36 (and proximally retract the deployment sheath 16 as described above), the external threads of the threaded rod 36 may engage a gear 44 coupled to the actuation member 20 (e.g., a thumbwheel). Accordingly, rotation of the actuation member 20 may result in the proximal retraction of the coupling member 46 and proximal retraction of the deployment sheath 16.

FIG. 3 further illustrates that the handle 14 may include a first handle member 14A and a second handle member 14B. It can be appreciated that the first handle member 14A may be designed to mate with the second handle member 14B to form the handle 14. In other words, the first handle member 14A may combine (e.g., engage) with the second handle member 14B in a clamshell configuration to form the handle 14.

It can be further appreciated from FIG. 3 that the handle 14 may include an inner chamber which houses various components of the medical device system 10. For example, when the first handle member 14A is combined with the second handle member 14B, the threaded rod 46 and the coupling member 46 may be positioned within the inner chamber of the handle 14. Further, it can be appreciated from the above discussion that the rotation of the threaded rod 36 and the translation of the coupling member 46 along the threaded rod may occur entirely within the inner chamber of the handle 14.

Figure 4:
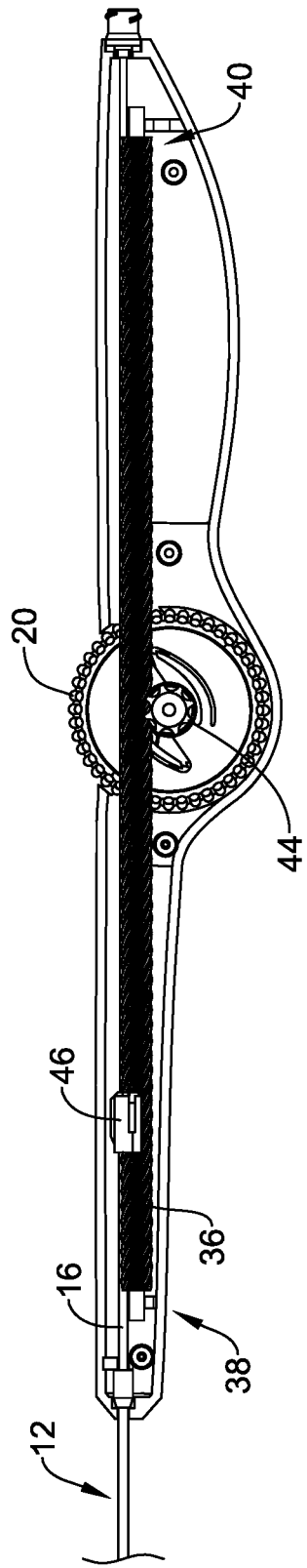
Figure 5:
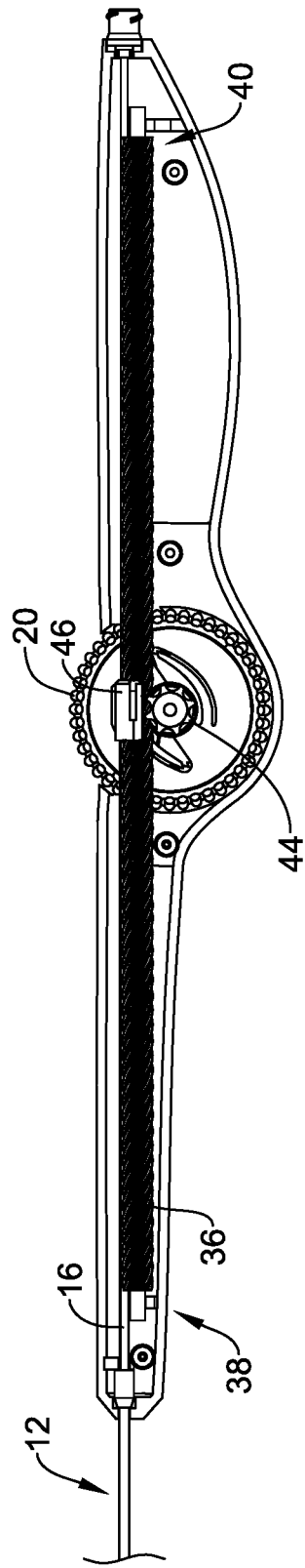
Figure 6:
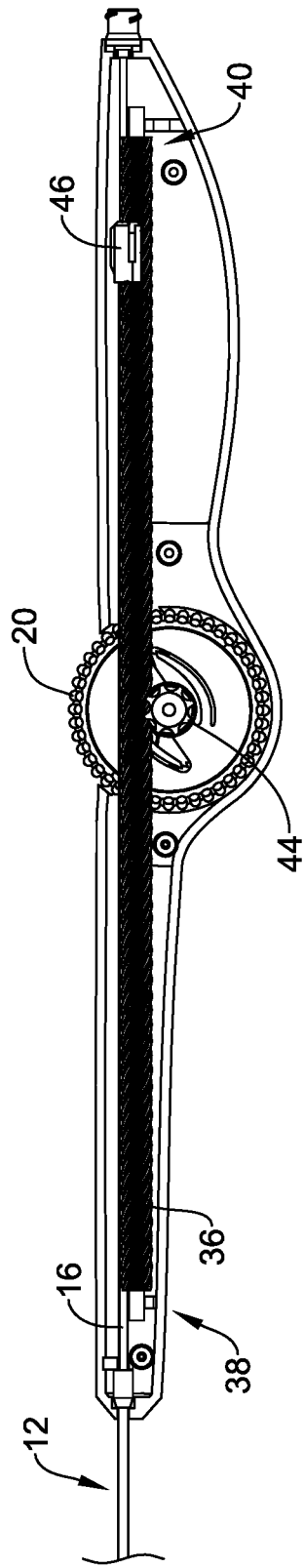

FIGS. 4-6 illustrate cross-sectional views showing the distal-to-proximal translation of the coupling member 46 along the threaded rod 36 as described above. For example, FIG. 4 illustrates the coupling member 46 positioned adjacent the distal end region 38 of the threaded rod 36. Further, FIG. 4 illustrates the deployment sheath 16 extending through the inner lumen of the shaft 12, whereby the proximal end of the deployment sheath 16 is attached to the coupling member 46 (it is noted that a portion of the deployment sheath 16 is not visible in FIG. 4 as it positioned "behind" the threaded rod 36 in the figure).

FIG. 4 further illustrates that the coupling member 46 may be positioned distal of the gear 44 (which is engaged to the actuation member 20, as described above) when the deployment sheath 16 is in a first configuration in which the deployment sheath is covering the stent (as described above). As will be illustrated below, as the actuation member 20 is actuated (e.g., the thumbwheel 20 is rotated), the gear 44 rotates the threaded rod 36. Further, rotation of the threaded rod 36 may translate the coupling member 46 in a distal-to-proximal direction, whereby the coupling member 46 may translate toward the proximal end region 40 of the threaded rod 36.

FIG. 5 illustrates the system 10 shown in FIG. 4 after the coupling member 46 has been translated in a distal-to-proximal direction along the threaded rod 36. Specifically, FIG. 5 illustrates the coupling member 46 having been translated in a distal-to-proximal direction such that the coupling member 46 is positioned adjacent to the gear 44 (which is engaged with the actuation member 20). In other words, it can be appreciated from FIG. 5 that as a clinician actuates the actuation member 20 (e.g., rotates the thumbwheel 20), the gear 44 (which is engaged with the actuation member 20) engages and rotates the threaded rod 36. Further, the rotation of the threaded rod 36 may translate the coupling member 46 from a position adjacent to the distal end region 38 of the threaded rod 36 toward the proximal end region 40 of the threaded rod 36. Additionally, as described above, the distal-to-proximal translation of the coupling member 46 may pull the deployment sheath 16 in a distal-to-proximal direction to partially uncover (e.g., partially deploy) the stent (as with FIG. 4, it is noted that a portion of the deployment sheath 16 is not visible in FIG. 5 as it positioned "behind" the threaded rod 36 in the figure).

FIG. 6 illustrates the system 10 shown in FIGS. 4-5 after the coupling member 46 has been further translated in a distal-to-proximal direction along the threaded rod 36. Specifically, FIG. 6 illustrates the coupling member 46 having been translated in a distal-to-proximal direction such that the coupling member 46 is positioned proximal to the gear 44 (which is engaged with the actuation member 20). In other words, it can be appreciated from FIG. 6 that as a clinician further actuates the actuation member 20 (as compared to FIG. 5), the gear 44 (which is engaged with the actuation member 20) engages and rotates the threaded rod 36. Further, the rotation of the threaded rod 36 may translate the coupling member 46 from a position adjacent the gear 44 further toward the proximal end region 40 of the threaded rod 36. Additionally, and as described above, the distal-to-proximal translation of the coupling member 46 may pull the deployment sheath 16 in a distal-to-proximal direction to fully uncover (e.g., fully deploy) the stent (as with FIGS. 4-5, it is noted that a portion of the deployment sheath 16 is not visible in FIG. 6 as it positioned "behind" the threaded rod 36 in the figure).

Figure 7:
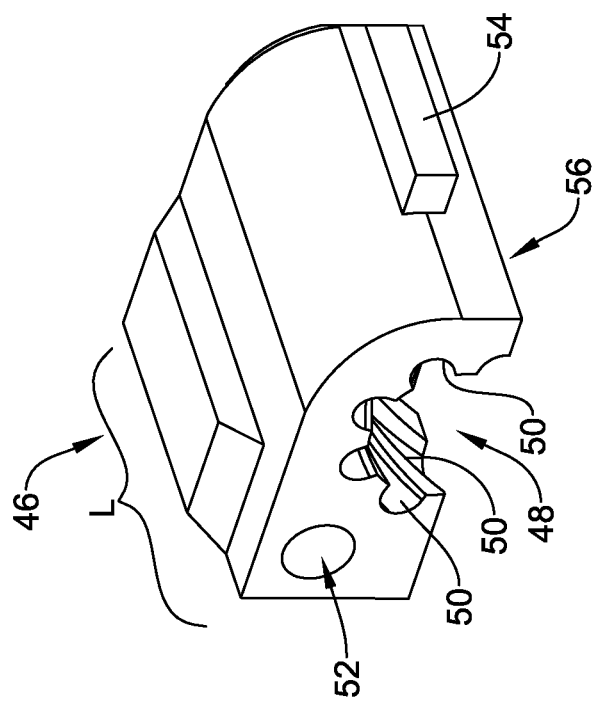
FIG. 7 illustrates a portion of an example stent delivery system.

FIG. 7 illustrates a perspective view of the coupling member 46 discussed above with respect to FIGS. 3-6. As shown in FIG. 7, the coupling member 46 may include an engagement portion 48. The engagement portion 48 may include one or more internal threads 50 extending from a bottom surface 56 of the coupling member 46. As discussed above, the internal threads 50 may be designed such that they engage the exterior threads of the threaded rod 36.

FIG. 7 further illustrates that the coupling member 46 may further include an aperture 52. The aperture 52 may extend through the entire length "L" of the coupling member 46. As discussed above, the aperture 52 may be designed such that the inner shaft 23 may extend therethrough. In other words, the diameter of the aperture 52 may be sized such that it is larger than the outer diameter of the inner shaft 23.

Further, in some examples, the aperture 52 may be sized to permit a portion of the proximal end of the deployment sheath 16 to be positioned therein. The proximal end of the deployment sheath 16 may be fixedly attached to the coupling member 46 in a variety of ways. For example, the proximal end of the deployment sheath 16 may be adhesively bonded to the coupling member 46. Further, it can be appreciated the proximal end of the deployment sheath 16 may be fixedly attached to the coupling member 46 using one or more additional components which may create an interference lock with the coupling member.

FIG. 7 further illustrates that the coupling member 46 may further include a flange 54 projecting outward from the surface of the coupling member 46. As will be described in greater detail below, the flange 54 may be utilized to orient the coupling member 46 in a particular arrangement with respect to the handle 14 and additional components of the medical system 10.

Figure 8:
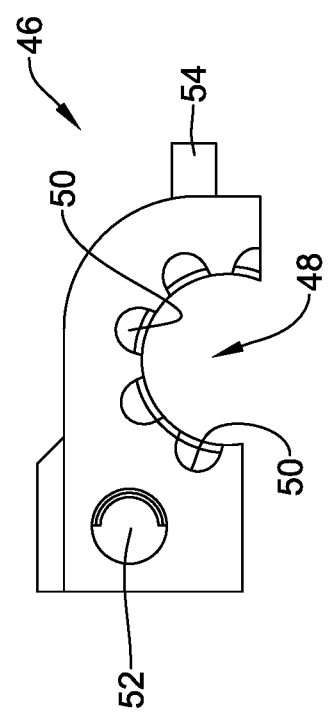
FIG. 8 illustrates a portion of an example stent delivery system.

FIG. 8 illustrates a front view of the coupling member 46 including the aperture 52, the engagement region 48 (including the internal threads 50) and the flange 54. Additionally, the front view of FIG. 8 illustrates that the engagement region 48 may be designed such that it resembles a half-moon shape. The half-moon shape of the engagement region 48 may be designed such that a bottom surface of the coupling member 46 substantially aligns with a midline of the threaded rod 36 when the coupling member 46 is engaged with threaded rod 36. It can be appreciated from FIG. 8 and the above discussion that designing the engagement region 48 to only partially surround the threaded rod 36 may permit the coupling member 46 to pass over the gear 44 (or other components of the system 10) when translating along the threaded rod 36.

Figure 9:
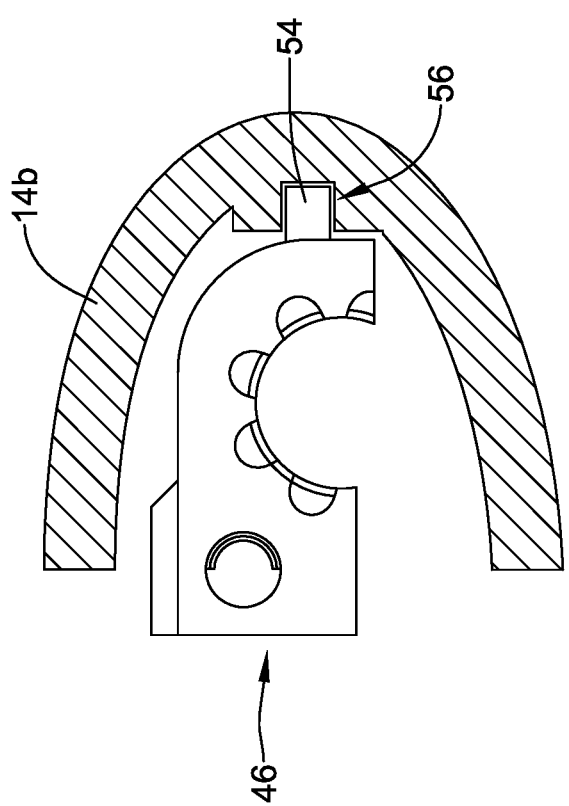
FIG. 9 illustrates a portion of an example stent delivery system.

FIG. 9 illustrates a front view of the coupling member 46 positioned adjacent to the second handle member 14B (the second handle member 14B is shown in cross-section in FIG. 9). As discussed above, in some instances it may be desirable to position the flange 54 into a channel 56 formed into the wall of the second handle member 14B. It can be appreciated that positioning the flange 54 into the channel 56 may orient the coupling member 46 in the position shown in FIG. 9. In other words, disposing the flange 54 into the channel 56 may maintain the coupling member 36 in a position whereby the engagement region 48 engages with the threads of the threaded rod 36 as described above. It can be further appreciated that the channel 56 may extend along the entire length of the second handle member 14B. However, this is not intended to be limiting. Rather, it can be further appreciated that the channel 56 may extend along only a portion of the second handle member 14B.

Figure 10:
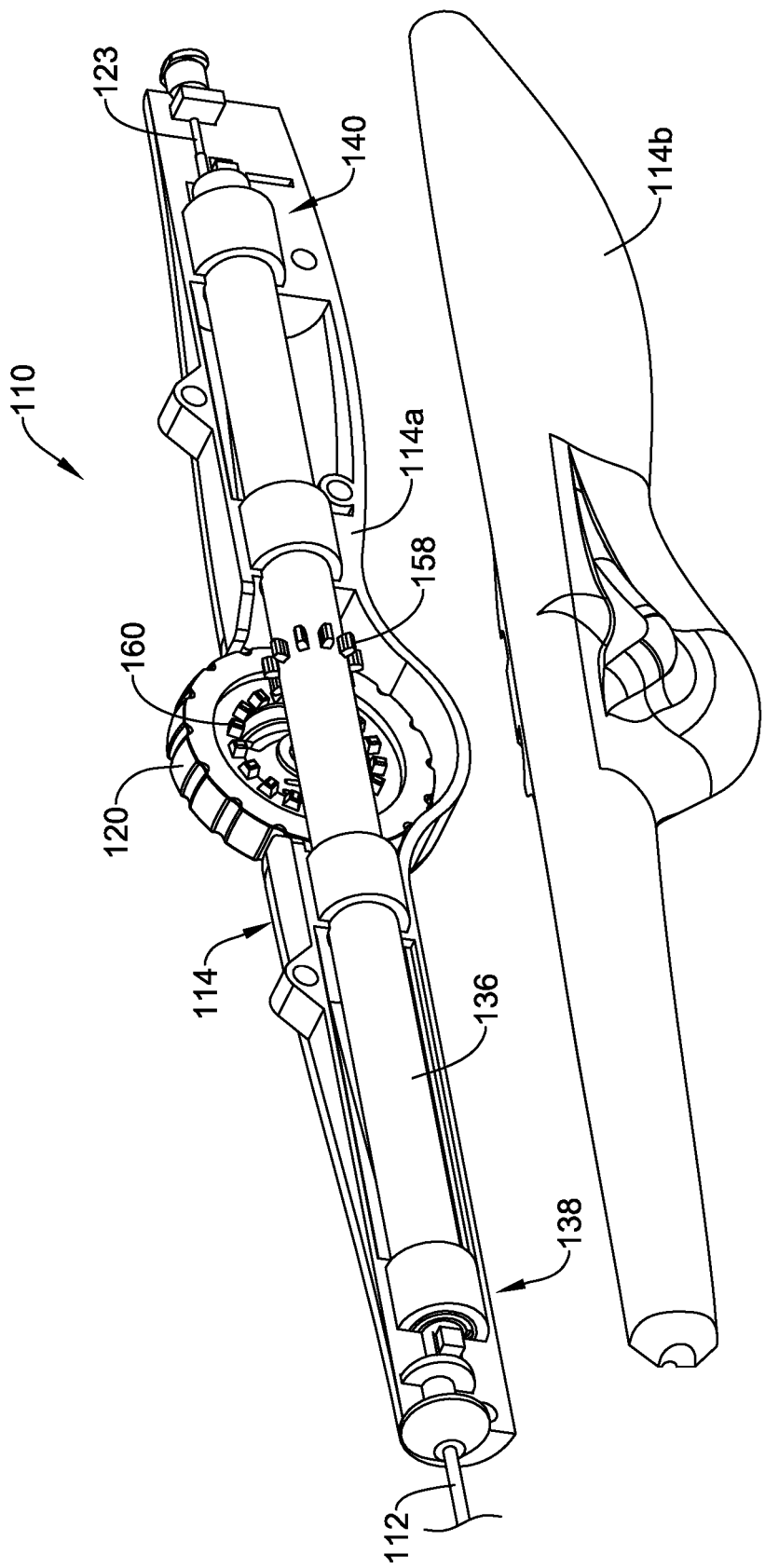
FIG. 10 illustrates a portion of another example stent delivery system.

FIG. 10 illustrates another example stent delivery system 110. The system 110 may be similar in form and function to the stent delivery system 10 described above. For example, the system 110 may include an actuation member 120 disposed within a first handle member 114A. Additionally, a second handle member 114B may be coupled with the first handle member 114A to form the handle 114. FIG. 10 further illustrates that the stent delivery system 110 may further include an internally-threaded rod 136. The internally-threaded rod 136 may be coupled to the actuation member 120 via the engagement of a plurality of projections 158 (extending radially away from the outer surface of the internally-threaded rod 136) with a plurality of receptacles 160 (disposed along the actuation member 120).

As will be described in greater detail below, the internally-threaded rod 136 may include an internal, female tread portion that may extend from a distal end region 138 of the internally-threaded rod 136 to a proximal end region 140 of the internally-threaded rod 136. Further, a coupling member 162 (not shown in FIG. 10 but visible in FIG. 11) may be disposed within the internally-threaded rod 136. The coupling member 162 may include a plurality of projections 166 (not shown in FIG. 10 but visible in FIG. 11) extending radially away from the outer surface of the shuttle. The projections 166 may engage with the internal thread of the internally-threaded rod 136. Accordingly, rotation of the internally-threaded rod 136 (via actuation of the actuation member 120) may translate the shuttle 162 along internally-threaded rod 136.

Similarly to the system 10 described above, FIG. 10 illustrates that the system 110 may include a shaft 112 coupled to the handle 114. The shaft 112 may be similar in form and function to the shaft 12 described above. Further, while not visible in FIG. 10 (but shown in FIG. 11), the shaft 112 may include a lumen extending therein through which a deployment sheath 116 (shown in FIG. 11) may extend. The deployment sheath 116 may be similar in form and function to the deployment sheath 16 described above. Additionally, FIG. 10 illustrates that the system 110 may include an inner shaft 123 (e.g., hypotube) which extends through the internally-threaded rod 136, the deployment sheath 116 and/or the shaft 112.

Figure 11:
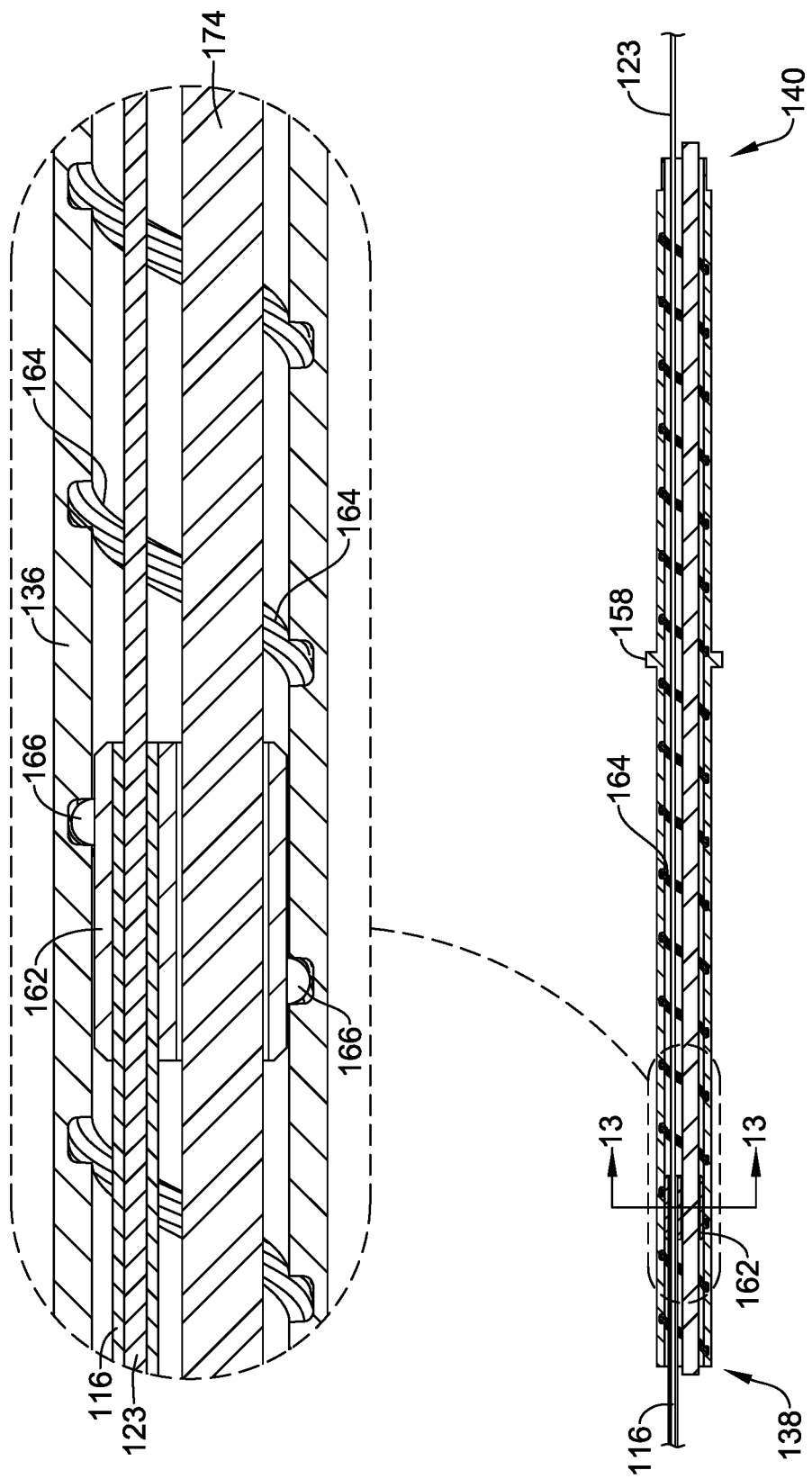
FIG. 11 illustrates a portion of an example stent delivery system.

FIG. 11 illustrates a partial cross-sectional view of the example stent system 110. Specifically, FIG. 11 illustrates a partial cross-section of the internally-threaded rod 136. Further, the detailed view of FIG. 11 illustrates the coupling member 162 disposed within the internally-threaded rod 136. FIG. 11 further illustrates the outwardly extending projections 166 disposed within the internal (female) thread 164. It can be appreciated from FIG. 11 that as the internally-threaded rod 136 rotates, the coupling member 162 may be translated as the internal thread 164 engages the projections 166 of the coupling member 162.

The detailed view of FIG. 11 further illustrates the deployment sheath 116 attached to the distal end of the coupling member 116. Additionally, the detailed view of FIG. 11 further illustrates the inner shaft 123 extending within the lumen of the deployment sheath 116. Further, the detailed view of FIG. 11 further illustrates the inner shaft 123 may extend through an aperture 170 (more clearly shown in FIG. 12) located in the coupling member 162. The inner shaft 123 may extend through the aperture 170 and attach to the proximal end region of the handle 114.

Figure 12:
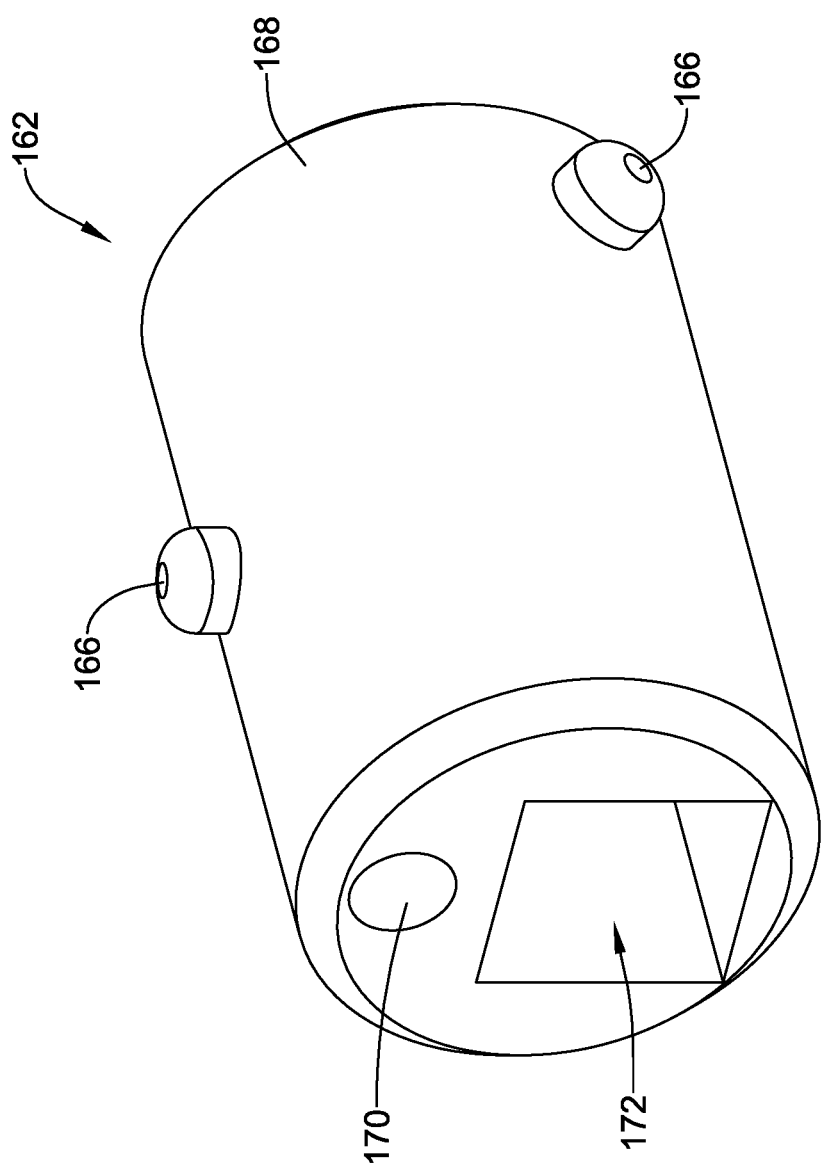
FIG. 12 illustrates a portion of an example stent delivery system.

FIG. 11 further illustrates that the system 110 may include an orientation rod 174 extending from the distal end region 138 of the internally-threaded rod 136 to a proximal end region 140 of the internally-threaded rod 136. The cross-sectional shape (e.g., profile) of the orientation rod 174 may be square (FIG. 12 shows the opening 172 for the orientation rod having a square profile), but this is not intended to be limiting. Rather, the cross-sectional shape could be rectangular, ovular, triangular, polygonal, or any other suitable geometric shape.

It can be appreciated that positioning the orientation rod 174 may orient the coupling member 162 in the position shown in FIG. 11. In other words, the orientation rod 174 may limit the ability of the coupling member 162 to rotate as it translates along the internally-threaded rod 136 as described above. It can be further appreciated that the orientation rod 174 may extend along the entire length of the handle member 114. However, this is not intended to be limiting. Rather, it can be further appreciated that the orientation rod 174 may extend along only a portion of the second handle member 114.

FIG. 12 illustrates a perspective view of the coupling member 162. As described above, FIG. 12 further illustrates two projections 166 extending away from the outer surface 168 of the coupling member 162. While FIG. 12 illustrates two projections 166 extending away from the outer surface 168, it is not intended to be limiting. Rather, it can be appreciated that the coupling member 162 may include 2, 3, 4, 5, 6 or more projections.

FIG. 12 further illustrates that the aperture 170 (through which the deployment sheath and/or inner member may extend) and the opening 172 through which the orientation rod extends. As discussed above, the orientation rod 174 may have a square cross-sectional shape.

Figure 13:
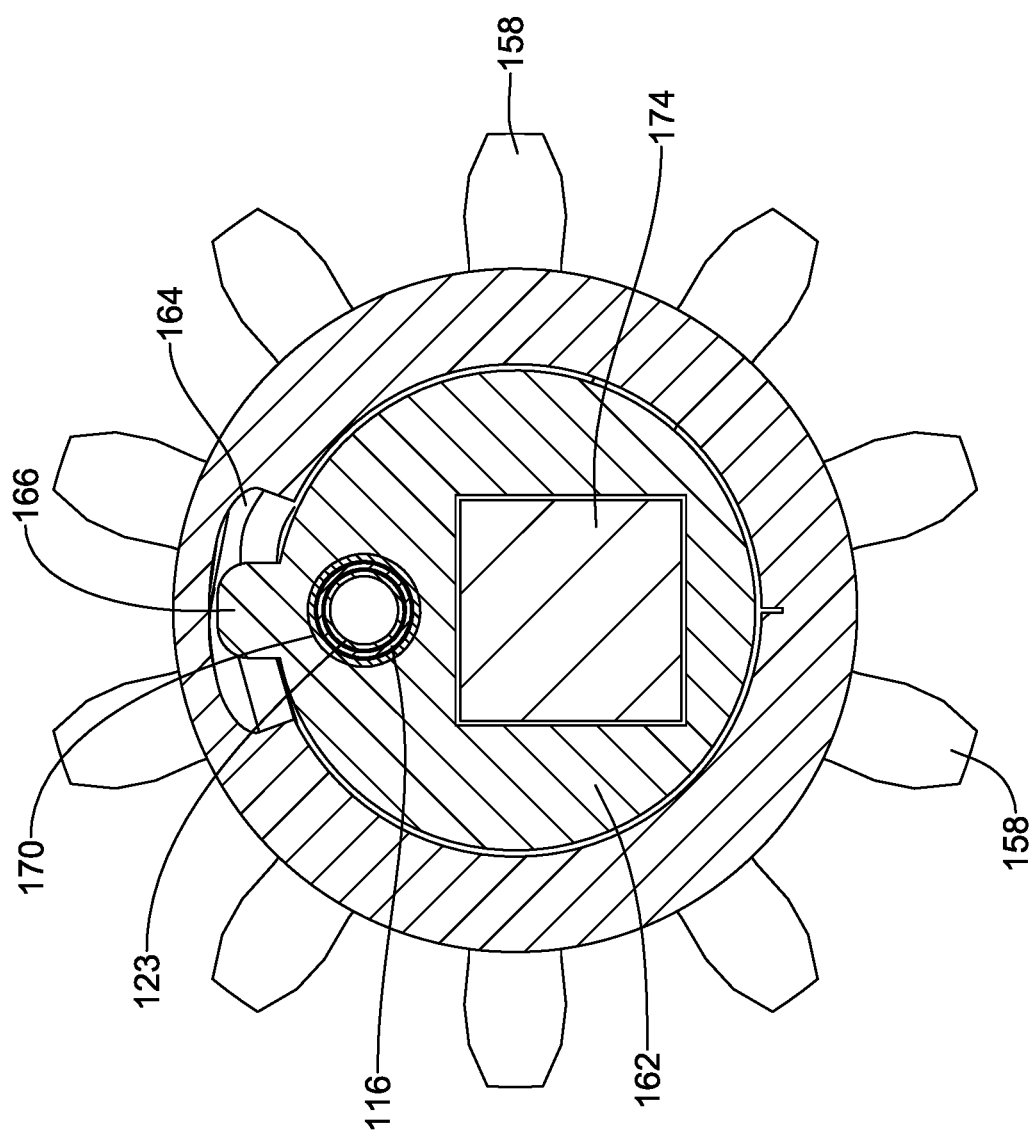
FIG. 13 illustrates a portion of an example stent delivery system.

FIG. 13 is a cross-section of the system 110 taken along line 13-13 of FIG. 11. FIG. 13 shows the coupling member 162 positioned within the internally-threaded rod 136. Further, FIG. 13 illustrates the projections 158 extending away from the outer surface of the rod 136. Additionally, FIG. 13 shows the deployment sheath 116 and the inner member 122 extending through aperture 170. FIG. 13 also shows a projection 166 positioned within the internal thread 164 and the orientation rod 174 (having a square shape as described above) extending within the coupling member 162.

While the above examples illustrate stent delivery systems in which a shaft (e.g., the deployment sheath 16 in system 10) is retracted in a distal-to-proximal direction to uncover and deploy a stent from its distal-to-proximal ends, other deployment configurations are contemplated. For example, one or more of the mechanisms described above may be utilized to deploy a stent in a proximal-to-distal manner. In other words, one or more of the above of the above mechanisms may be utilized to advance a deployment sheath in a proximal-to-distal direction, and thereby deploy a stent from its proximal end to its distal end. Examples of stent delivery systems in which a stent is deployed from its proximal end to its distal end are disclosed in U.S. Patent Application Pub. No. 2016/0128857, the entirety of which is incorporated by reference.

Figure 14:
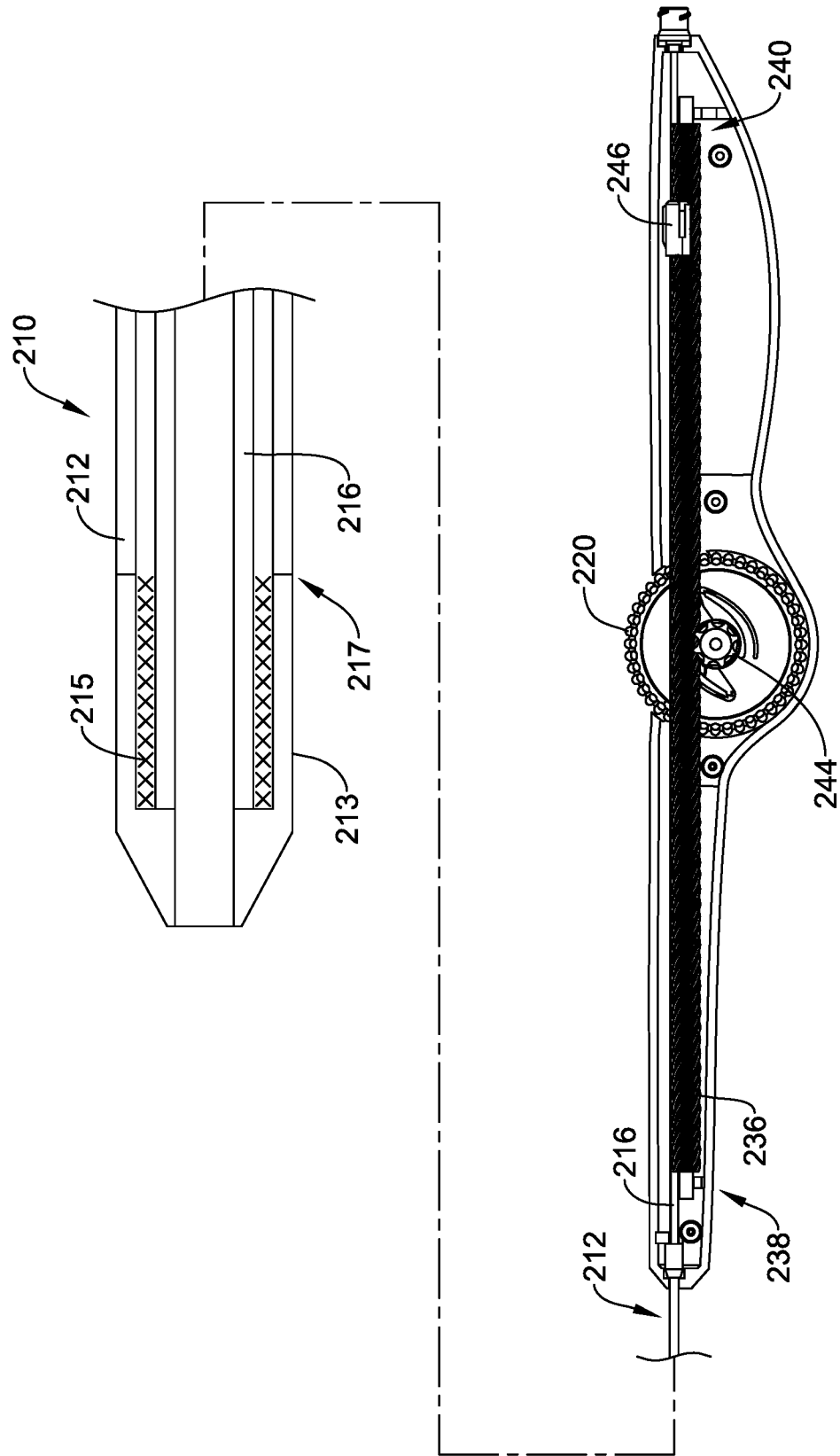
FIG. 14 illustrates a portion of another example stent delivery system.

To that end, FIG. 14 illustrates another example stent system 210. The stent system 210 shows a handle system (similar to the handle system shown in FIG. 6), whereby the coupling member 246 (similar to the coupling member 46 in FIG. 6) is positioned along a proximal end region 240 of the threaded rod 236 (similar to the threaded rod 36 in FIG. 6). It can be appreciated that the threaded rod 236 may be rotated by actuating the actuation member 220 (similar to the actuation member 20), whereby the actuation member 220 is coupled to the threaded rod 236 via the gear 244. As will be shown in FIG. 15, rotation of the threaded rod 236 via the actuation member 220 may translate the coupling member 246 in a proximal-to-distal direction from a proximal end region 240 toward the distal end region 238 of the threaded rod 236.

FIG. 14 further illustrates that the system 210 may include any outer sheath 212 abutting a tip member 213. The location at which the distal end of the sheath 212 abuts the proximal end of the tip member 213 is depicted by the reference numeral 217 in FIG. 14. Further, as shown in FIG. 14, the tip member 213 may be configured such that it covers an expandable stent 215. Additionally, FIG. 14 illustrates a deployment shaft 216 which may extend through a lumen of the sheath 212. A distal end of the deployment sheath 216 may be coupled to the tip member 213 and the proximal end of the deployment sheath 216 may be coupled to the coupling member 246.

Figure 15:
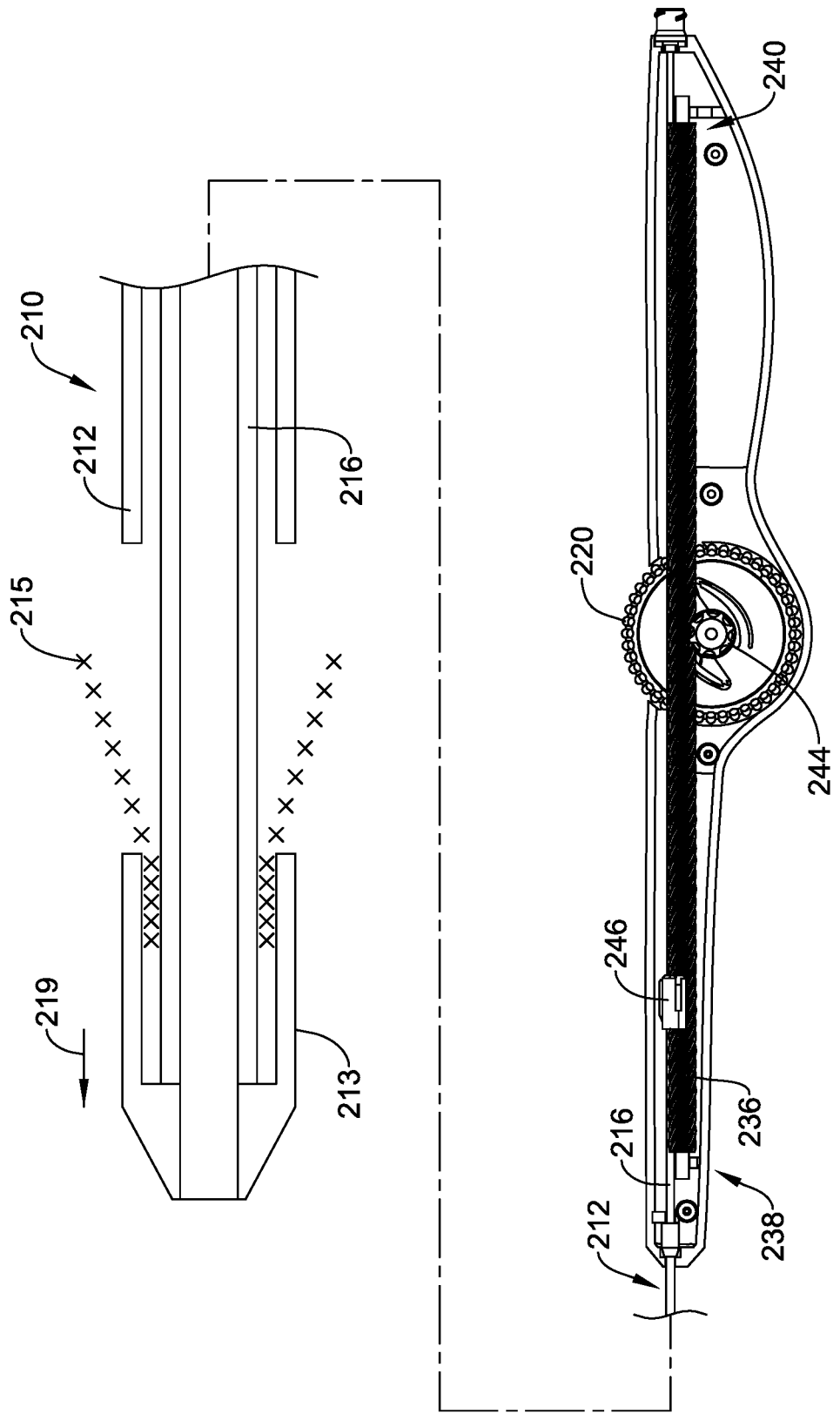
FIG. 15 illustrates a portion of another example stent delivery system.

FIG. 15 illustrates the system 210 after the actuation member 220 has been actuated such that the threaded rod 236 rotates and the coupling member 246 has been translated from the proximal end region 240 toward the distal end region 236 of the threaded rod 236. As can be appreciated from the above discussion, the coupling member 246 may pass directly over the gear 244 when translating from the proximal end region 240 toward the distal end region 238 of the threaded rod 236.

Additionally, FIG. 15 illustrates that the proximal-to-distal translation of the coupling member 246 may shift the deployment shaft 216 in a proximal-to-distal direction. Further, the proximal-to-distal translation of the deployment shaft 216 may translate the tip member 213 in a proximal-to-distal direction, as shown by the arrow 219. The proximal-to-distal translation of the tip member 213 may first uncover and deploy a proximal end of the stent 215, followed by the progressive deployment of the stent 215 in a proximal to distal direction.

The materials that can be used for the various components of the system 10 (and/or other systems disclosed herein) may include those commonly associated with medical devices. However, this is not intended to limit the devices and methods described herein, as the discussion may be applied to other components, devices, or systems disclosed herein.

The components of the system 10 (and/or other systems disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the components of the system 10 (and/or other systems disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the components of the system 10 (and/or other systems disclosed herein) in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the components of the system 10 (and/or other systems disclosed herein) to achieve the same result.

In some embodiments, a degree of Magnetic Resonance Imaging (MRI) compatibility is imparted into the system 10 (and/or other systems disclosed herein). For example, components of the system 10 (and/or other systems disclosed herein), may be made of a material that does not substantially distort the image and create substantial artifacts (e.g., gaps in the image). Certain ferromagnetic materials, for example, may not be suitable because they may create artifacts in an MRI image. The components of the system 10 (and/or other systems disclosed herein) or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A stent delivery system, comprising:
   an inner member having a first longitudinal axis;
   a deployment sheath axially slidable relative to the inner member;
   a handle coupled to the deployment sheath, wherein the handle includes a proximal end region, a distal end region and a medial region extending from the distal end region to the proximal end region;
   a rod coupled to the handle, the rod having a distal end region, a proximal end region, and a second longitudinal axis;
   a thumbwheel coupled to both the handle and the rod, wherein the thumbwheel is positioned along the medial region of the handle, and wherein actuation of the thumbwheel is configured to rotate the rod along the second longitudinal axis; and
   a coupling member configured to couple the rod to the deployment sheath;

wherein the first longitudinal axis is offset from the second longitudinal axis.

2. The stent delivery system of claim 1, wherein the coupling member includes an aperture, and wherein the inner member is designed to extend within the aperture.

3. The stent delivery system of claim 1, wherein rotation of the rod is designed to translate the coupling member along the rod.

4. The stent delivery system of claim 3, wherein the rod includes a first threaded portion extending from the distal end region to the proximal end region.

5. The stent delivery system of claim 4, wherein the coupling member includes an engagement portion, and wherein the first threaded portion of the rod is designed to engage the engagement portion of coupling member.

6. The stent delivery system of claim 5, wherein the engagement portion of the coupling member includes a second threaded portion.

7. The stent delivery system of claim 6, wherein the first threaded portion includes an external thread, and wherein the second threaded portion includes an internal thread, and wherein the external thread is configured to engage with the internal thread.

8. The stent delivery system of claim 5, wherein the engagement portion of the coupling member includes at least one projection extending radially outward from an outer surface of the coupling member.

9. The stent delivery system of claim 8, wherein the first threaded portion includes an internal thread, and wherein the at least one projection of the coupling member is configured to engage with the internal thread.

10. A stent delivery system, comprising:
an inner member having a stent receiving region;
a stent disposed along the stent receiving region;
a deployment sheath axially slidable relative to the inner member;
a handle coupled to the deployment sheath, wherein the handle includes a proximal end region, a distal end region and a medial region extending from the distal end region to the proximal end region;
a rod coupled to the handle, the rod having a distal end region and a proximal end region;
a thumbwheel coupled to both the handle and the rod, wherein the thumbwheel is positioned along the medial region of the handle, and wherein actuation of the thumbwheel is configured to rotate the rod along a longitudinal axis of the rod; and
a coupling member configured to couple the rod to the deployment sheath;
wherein the inner member is non-coaxially positioned relative to the rod.

11. The stent delivery system of claim 10, wherein the coupling member includes an aperture, and wherein the inner member is designed to extend within the aperture.

12. The stent delivery system of claim 11, wherein coupling member is configured to translate relative to the inner member.

13. The stent delivery system of claim 10, wherein rotation of the rod is designed to translate the coupling member along the rod.

14. The stent delivery system of claim 13, wherein the coupling member is configured to translate along the rod from the distal end region to the proximal end region, and wherein the translation of the coupling member pulls the deployment sheath proximally to deploy the stent.

15. The stent delivery system of claim 10, wherein the rod includes a first threaded portion extending from the distal end region to the proximal end region.

16. The stent delivery system of claim 15, wherein the coupling member includes an engagement portion, and wherein the first threaded portion of the rod is designed to engage the engagement portion of coupling member.

17. The stent delivery system of claim 15, wherein the engagement portion of the coupling member includes a second threaded portion.

18. A stent delivery system, comprising:
an inner member having a stent receiving region and a first longitudinal axis;
a stent disposed along the stent receiving region;
a deployment sheath axially slidable relative to the inner member;
a handle coupled to the deployment sheath, wherein the handle includes a proximal end region, a distal end region and a medial region extending from the distal end region to the proximal end region;
a rod coupled to the handle, the rod having a distal end region and a proximal end region, wherein the inner member is non-coaxially positioned relative to the rod;
a thumbwheel coupled to both the handle and the rod, wherein the thumbwheel is positioned along the medial region of the handle, and wherein actuation of the thumbwheel is configured to rotate the rod along a longitudinal axis of the rod; and
a coupling member configured to couple the rod to the deployment sheath, wherein rotation of the rod is designed to shift the coupling member from a first configuration in which the deployment sheath covers the stent to a second configuration in which the deployment sheath uncovers the stent.

* * * * *